(12) United States Patent
Rees et al.

(10) Patent No.: US 11,406,965 B2
(45) Date of Patent: Aug. 9, 2022

(54) CATALYST AND PROCESS USING THE CATALYST FOR MANUFACTURING FLUORINATED HYDROCARBONS

(71) Applicant: MEXICHEM FLUOR S.A. DE C.V., San Luis Potosi (MX)

(72) Inventors: Claire Nicola Rees, Runcorn (GB); Claire Elizabeth McGuinness, Runcorn (GB); Andrew Paul Sharratt, Runchorn (GB)

(73) Assignee: Mexichem Fluor S.A. de C.V., San Luis Potosi (MX)

( * ) Notice: Subject to any disclaimer, the term of this patent is extended or adjusted under 35 U.S.C. 154(b) by 0 days.

(21) Appl. No.: 16/331,259

(22) PCT Filed: Sep. 7, 2017

(86) PCT No.: PCT/GB2017/052618
§ 371 (c)(1),
(2) Date: Mar. 7, 2019

(87) PCT Pub. No.: WO2018/046928
PCT Pub. Date: Mar. 15, 2018

(65) Prior Publication Data
US 2019/0217276 A1    Jul. 18, 2019

(30) Foreign Application Priority Data
Sep. 7, 2016 (GB) .................................... 1615209

(51) Int. Cl.
*B01J 23/26*    (2006.01)
*B01J 37/02*    (2006.01)
(Continued)

(52) U.S. Cl.
CPC ............. *B01J 23/26* (2013.01); *B01J 23/002* (2013.01); *B01J 23/28* (2013.01); *B01J 23/866* (2013.01);
(Continued)

(58) Field of Classification Search
None
See application file for complete search history.

(56) References Cited

U.S. PATENT DOCUMENTS

| 231,840 A | 8/1880 | Neahous |
| 2,700,686 A | 1/1955 | Dickey et al. |

(Continued)

FOREIGN PATENT DOCUMENTS

| CN | 104475080 A | 4/2015 |
| CN | 105688890 | 6/2016 |

(Continued)

OTHER PUBLICATIONS

English translation of Patent No. RU2555842, Jul. 10, 2015, pp. 1-10 (Year: 2015).*

(Continued)

*Primary Examiner* — Colin W. Slifka
(74) *Attorney, Agent, or Firm* — Crowell & Moring LLP

(57) ABSTRACT

A catalyst comprising chromia and at least one additional metal or compound thereof and wherein the catalyst has a total pore volume of greater than 0.3 cm$^3$/g and the mean pore diameter is greater than or equal to 90 Å, wherein the total pore volume is measured by N2 adsorption porosimetry and the mean pore diameter is measured by $N_2$ BET adsorption porosimetry, and wherein the at least one additional metal is selected from Li, Na, K, Ca, Mg, Cs, Sc, Al, Y, Ti, Zr, Hf, V, Nb, Ta, Cr, Mo, W, Mn, Re, Fe, Ru, Co, Rh, Ir, Ni, Pd, In, Pt, Cu, Ag, Au, Zn, La, Ce and mixtures thereof.

46 Claims, 6 Drawing Sheets

(51) Int. Cl.

| | | |
|---|---|---|
| *B01J 37/03* | (2006.01) | |
| *B01J 37/04* | (2006.01) | |
| *B01J 37/08* | (2006.01) | |
| *B01J 37/26* | (2006.01) | |
| *B01J 23/86* | (2006.01) | |
| *B01J 27/132* | (2006.01) | |
| *B01J 35/02* | (2006.01) | |
| *B01J 35/10* | (2006.01) | |
| *B01J 37/00* | (2006.01) | |
| *C07C 17/21* | (2006.01) | |
| *C07C 17/25* | (2006.01) | |
| *B01J 23/00* | (2006.01) | |
| *B01J 27/12* | (2006.01) | |
| *C07C 17/20* | (2006.01) | |
| *B01J 23/28* | (2006.01) | |
| *C07C 17/08* | (2006.01) | |

(52) U.S. Cl.
CPC ............ *B01J 27/12* (2013.01); *B01J 27/132* (2013.01); *B01J 35/023* (2013.01); *B01J 35/026* (2013.01); *B01J 35/1019* (2013.01); *B01J 35/1038* (2013.01); *B01J 35/1042* (2013.01); *B01J 35/1061* (2013.01); *B01J 37/0009* (2013.01); *B01J 37/0236* (2013.01); *B01J 37/033* (2013.01); *B01J 37/04* (2013.01); *B01J 37/088* (2013.01); *B01J 37/26* (2013.01); *C07C 17/08* (2013.01); *C07C 17/20* (2013.01); *C07C 17/21* (2013.01); *C07C 17/25* (2013.01); *B01J 2523/00* (2013.01)

(56) References Cited

U.S. PATENT DOCUMENTS

| | | | |
|---|---|---|---|
| 2,889,379 A | 6/1959 | Ruh et al. | |
| 2,918,501 A | 12/1959 | Brehm et al. | |
| 2,931,840 A | 4/1960 | Marquis | |
| 2,996,555 A | 8/1961 | Rausch | |
| 3,000,979 A | 9/1961 | Gibbs | |
| 3,398,204 A | 8/1968 | Gallant | |
| 3,674,665 A | 7/1972 | Cristol et al. | |
| 3,739,036 A | 6/1973 | Valicenti et al. | |
| 3,793,229 A | 2/1974 | Groppelli et al. | |
| 4,093,670 A | 6/1978 | Ozawa et al. | |
| 4,188,284 A | 2/1980 | Quick et al. | |
| 4,220,608 A | 9/1980 | Feiring | |
| 4,465,786 A | 8/1984 | Zimmer et al. | |
| 4,798,818 A | 1/1989 | Baizer et al. | |
| 5,672,803 A | 9/1997 | Smith et al. | |
| 5,679,875 A | 10/1997 | Aoyama et al. | |
| 5,763,711 A | 6/1998 | Ito | |
| 5,811,603 A | 9/1998 | Elsheikh | |
| 5,856,593 A | 1/1999 | Powell et al. | |
| 5,986,151 A | 11/1999 | Van Der Puy | |
| 6,111,150 A | 8/2000 | Sakyu et al. | |
| 6,124,510 A | 9/2000 | Elsheikh et al. | |
| 6,329,559 B1 | 12/2001 | Sievert et al. | |
| 6,734,332 B1 | 5/2004 | Slaugh et al. | |
| 2004/0049088 A1* | 3/2004 | Lacroix .................. | B01J 23/866 570/166 |
| 2004/0167015 A1 | 8/2004 | Cann et al. | |
| 2005/0038302 A1 | 2/2005 | Hedrick et al. | |
| 2005/0090698 A1 | 4/2005 | Merkel et al. | |
| 2005/0228202 A1 | 10/2005 | Nappa et al. | |
| 2006/0122441 A1 | 6/2006 | Tung | |
| 2006/0269484 A1 | 11/2006 | Knopeck et al. | |
| 2007/0004585 A1 | 1/2007 | Amos et al. | |
| 2007/0100175 A1 | 5/2007 | Miller et al. | |
| 2007/0112230 A1 | 5/2007 | Mukhopadhyay et al. | |
| 2007/0129579 A1 | 6/2007 | Wang et al. | |
| 2007/0197842 A1 | 8/2007 | Mukhopadhyay et al. | |
| 2008/0051611 A1 | 2/2008 | Wang et al. | |
| 2009/0118554 A1 | 5/2009 | Rao et al. | |
| 2009/0209792 A1* | 8/2009 | Sharratt .................. | C07C 17/21 570/165 |
| 2010/0072415 A1 | 3/2010 | Rao et al. | |
| 2010/0268002 A1 | 10/2010 | Nose et al. | |
| 2011/0060111 A1 | 3/2011 | Cann et al. | |
| 2011/0118513 A1 | 5/2011 | Smith et al. | |
| 2011/0160497 A1 | 6/2011 | Deur-Bert et al. | |
| 2013/0303812 A1 | 11/2013 | Birke et al. | |

FOREIGN PATENT DOCUMENTS

| | | | |
|---|---|---|---|
| DE | 1140928 | 12/1962 | |
| DE | 2128341 | 6/1971 | |
| DE | 69406525 | 6/1995 | |
| EP | 0393517 A2 | 10/1990 | |
| EP | 0270006 | 2/1991 | |
| EP | 0502605 | 9/1992 | |
| EP | 0436989 | 3/1995 | |
| EP | 0644173 | 3/1995 | |
| EP | 0657408 A1 | 6/1995 | |
| EP | 0726243 | 8/1996 | |
| EP | 0752403 | 1/1997 | |
| EP | 0773061 | 5/1997 | |
| EP | 0957074 | 11/1999 | |
| EP | 0939071 | 7/2003 | |
| EP | 1350564 | 10/2003 | |
| EP | 1502906 | 2/2005 | |
| EP | 0957074 | 1/2006 | |
| EP | 1067106 | 4/2006 | |
| EP | 1900716 | 3/2008 | |
| EP | 1918269 | 5/2008 | |
| EP | 1877181 | 6/2015 | |
| EP | 1877181 B1 | 6/2015 | |
| EP | 3 330 244 B1 | 1/2020 | |
| FR | 2342952 | 9/1977 | |
| GB | 1407696 | 9/1975 | |
| GB | 1415649 | 11/1975 | |
| GB | 2011463 A1 | 11/1979 | |
| GB | 2162082 | 1/1986 | |
| GB | 1615197.9 | 10/2016 | |
| JP | S54-116004 | 9/1979 | |
| JP | H02-280837 | 11/1990 | |
| JP | H4345948 | 12/1992 | |
| JP | 07-206728 | 8/1995 | |
| JP | H1114002 | 5/1999 | |
| JP | 2006-111611 A | 4/2006 | |
| JP | 2006111611 A * | 4/2006 | ........... C07C 17/206 |
| JP | 2012-501826 | 1/2012 | |
| KR | 10-2011-0004431 | 1/2011 | |
| KR | 10-2011-0004434 | 1/2011 | |
| KR | 10-1343471 | 5/2011 | |
| KR | 10-1343618 | 5/2011 | |
| RU | 2322291 C1 | 4/2008 | |
| RU | 2402378 C1 | 10/2010 | |
| RU | 2431524 C1 | 10/2011 | |
| RU | 2555842 C1 * | 7/2015 | |
| WO | WO1993/004025 | 3/1993 | |
| WO | WO-9325507 A1 * | 12/1993 | ........... C07C 17/206 |
| WO | WO1996/011896 | 4/1996 | |
| WO | WO1997/005089 | 2/1997 | |
| WO | WO1998/010862 | 3/1998 | |
| WO | WO1998/033756 | 8/1998 | |
| WO | WO1998/037043 | 8/1998 | |
| WO | WO1999/062857 | 12/1999 | |
| WO | WO2004/018095 | 3/2004 | |
| WO | WO2005/012212 | 2/2005 | |
| WO | WO2005/023984 | 3/2005 | |
| WO | WO2005/037431 | 4/2005 | |
| WO | WO2005/037743 | 4/2005 | |
| WO | WO2005/037744 | 4/2005 | |
| WO | WO2005/042451 | 5/2005 | |
| WO | WO2005/108332 | 11/2005 | |
| WO | WO2005/108333 | 11/2005 | |
| WO | WO2005/108334 | 11/2005 | |
| WO | WO2006/106353 | 10/2006 | |
| WO | WO2007/056194 | 5/2007 | |
| WO | WO2007/079431 | 7/2007 | |
| WO | WO2007/079435 | 7/2007 | |

(56) References Cited

FOREIGN PATENT DOCUMENTS

| WO | WO2007/145171 | 12/2007 |
| WO | WO2007/0145171 | 12/2007 |
| WO | WO2008/002500 | 1/2008 |
| WO | WO2008/008350 | 1/2008 |
| WO | WO2008/030443 | 3/2008 |
| WO | WO2008/040969 | 4/2008 |
| WO | WO2008/054781 | 5/2008 |
| WO | WO2008/054782 | 5/2008 |
| WO | WO2008/075017 | 6/2008 |
| WO | 2009/125200 A2 | 10/2009 |
| WO | 2009125199 A2 | 10/2009 |
| WO | 2009125201 A2 | 10/2009 |
| WO | WO2009/140563 | 11/2009 |
| WO | 2010026382 A2 | 11/2010 |
| WO | 2010026383 A2 | 11/2010 |
| WO | WO2011/140013 | 10/2011 |
| WO | WO2011/140013 | 11/2011 |
| WO | 2015/046345 | 4/2015 |
| WO | WO 2018/046927 A1 | 3/2018 |

OTHER PUBLICATIONS

Ono et al, JP 2006-111611 A, English Translation from J-Plat Pat (Year: 2006).*
Burton et al.; Fluorine Chem, 44(1), 1989, pp. 167-174.
Haszeldine et al., J. Chem. Soc., "Fluoro-Olefins. Part II, Symthesis and Reactions of Some 3:3:3-trihalogenpropenes", 1953; pp. 3371-3378.
Sianesi et al., Fluoroolefins-Report 1 Cis and trans 1,2,3,3,3-pentafluoropropylene, Soc Montecatini Milan, Ann Chim (Rome) 55(8-9),1965; pp. 850-861.
Banks et al. J. Fluorine Chem, vol. 82, 1997; pp. 171-174.
Buchner et al., Chemistry: A European Journal, vol. 4, 1998, pp. 1799-1809.
Joyce et al.; J. Am. Chem, Soc., 1948; pp. 2529-2532.
Haszeldine et al., J. Chem. Soc. Perkin Trans 1, 1979; pp. 1943-1947.
Haszeldine et al., J. Chem Soc. 1970; pp. 414-421.
Haszeldine et al., J. Chem, Soc. Perkin Trans, 1, 1974; pp. 1303-1307.
Haszeldine et al.; J. Chem So. Perkin Trans 1.; 1976; pp. 2349-2353.
Meyer et al., Synthesis, 2000; pp. 1479-1490.
Atherton et al., J. Chem. Soc., 1971; pp. 366-371.
Boche et al., Chem. Ber., 1981; pp. 4005-4009 (no English Equivalent).
Baklouti et al., J. Flourine Chem. 1981; pp. 181-190 (no English Equivalent).
M. B. Smith and J. March, Advanced Organic Chemistry, Reaction, Mechanisms, and Structure, 5th Edition, p. 1195; 2001.
Search Report cited in PCT/GB2017/052618 dated Dec. 12, 2017.
Written Opinion cited in PCT/GB2017/052618 dated Mar. 15, 2018.
He Yongjun, Synthesis And Catalytic Properties of Nano Oxides, Shaanxi Science & Technology Press, pp. 8-11.
Catalysts Studies on Fluorination from 2-chloro-3,3,3-trifluoropropene to tetrafluoropropene (HFC-1234yf, HFC-1234ze), Zunyun Xie, "Chinese Master's Theses Full-text Database Engineering Science and Technology I", No. 3, 2014, B014-232.
Solid Catalyst, Xiang Dehui, pp. 342-344, Chemical Industrial Press.
Design and Preparation of Solid Catalyst, Pan Lvrang, pp. 137-138, Nankai University Press.
Elementary Chemical Engineering, Wang Dingjin, pp. 337-339, Higher Education Press.
Office Action for corresponding Chinese application 201780061867.X, dated Jun. 17, 2021, 20 pgs.
English Translation of Office Action for corresponding Chinese application 201780061867.X, dated Jun. 17, 2021, 17 pgs.
Office Action for corresponding Chinese application 201780065320.7, dated Jul. 2, 2021, 21 pgs.
English Translation of Office Action for corresponding Chinese application 201780065320.7, dated Jul. 2, 2021, 16 pgs.
Notice of Opposition in Europe Application No. 17768203.6, dated Aug. 9, 2021, 32 pages.
Notice of Opposition in Europe Application No. 17768204.4, dated Aug. 9, 2021, 34 pages.
D1 Thesis Hadar Rotter, "Development & Testing the Nanostructured Transition Metal Oxides in Combustion of Volatile Organic Compounds," Mar. 2006, 9 pages.
D2 Rama Rao et al., "Influence of Method of Preparation on Pore Structure and Deydrogenation of Activity of Chromia Catalysts", Indian Journal of Chemistry, dated Aug. 1996, vol. 35 A, Aug. 1996, pp. 656-659, 4 pages.
D3 Petrov et al., "Effect of Chromium Content on the Properties of a Alumina-Chromia Catalyst in Tetrachlorethylene Hydrofluorination", AIP Conference Proceedings 1772.030009 (2016), (cited Oct. 13, 2016), 6 pages.
D4 (Ru 2431524 C1) and D4a, Google machine translation of RU 2431524 C1, dated Oct. 20, 2011, 36 pages.*.
D5 (Ru 2402378 C1) and D5a Google machine translation of RU 2402378 C1, dated Oct. 27, 2010, 36 pages.*.
D6 (RU 2322291 C1) and D6a Google machine translation of RU 2322291 C1, dated Apr. 20, 2008, 30 pages.*.
D10 Rouquerol et al. "Recommendations for the Characterization of Porous Solids (Technical Report)", Pure & Appl. Chem. vol. 66, No. 8, 1994, pp. 1739-1758, International Union of Pure and Applied Chemistry, 20 pages.
D11 Thommes et al., Physisorption of Gases, with Special Reference to the Evaluation of Surface area and Pore Size Distribution (IUPAC Technical Report), Pure Appl. Chem. 2015, vol. 87, Nos. 9-10, pp. 1051-1069, Aug. 2015, 19 pages.

* cited by examiner

CATALYST AND PROCESS USING THE CATALYST FOR MANUFACTURING FLUORINATED HYDROCARBONS

RELATED APPLICATIONS

This application is a U.S. National Phase entry under 35 U.S.C. § 371 of International Application No. PCT/GB2017/052618, filed 7 Sep. 2017, which claims the benefit of Great Britain Patent Application No. 1615209.2, filed 7 Sep. 2016, the contents of each of which are incorporated herein by reference in their entireties.

The invention relates to a catalyst, a method of preparing said catalyst and to a process that uses said catalyst. More particularly, the invention relates to a catalyst comprising chromia and an additional metal and processes for using said catalyst in the addition or removal of halogen and halogen hydrides to/from compounds containing from 2 to 3 carbon atoms.

The listing or discussion of a prior published document in this specification should not necessarily be taken as an acknowledgement that the document is part of the state of the art or is common general knowledge.

Halocarbon-based compounds, particularly fluorocarbon-based compounds are currently used in a large number of commercial and industrial applications, such as propellants, blowing agents and heat transfer fluids. The interest in and use of fluorine-based compounds, particularly (hydro)fluoroolefins, as heat transfer fluids has increased as new refrigerants are sought.

(Hydro)haloalkenes such as hydrofluoropropenes can be conveniently prepared from corresponding hydro(halo)fluoroalkanes by dehydrohalogenation. The transformation can be effected thermally, i.e. by pyrolysis, catalytically, by contacting a hydro(halo)fluoroalkane with a catalyst under suitable conditions, or chemically, typically by contacting a hydro(halo)fluoroalkane with strong bases such as alkali metal hydroxides. For commercial operation, catalytic dehydrohalogenation is believed to be preferred.

The hydrofluoropropene 1,1,1,2,3-pentafluoropropene (HFO-1225ye), for example, can be prepared by contacting and dehydrofluorinating 1,1,1,2,3,3-hexafluoropropane in the gaseous state with trivalent chromium oxide or partially fluorinated trivalent chromium oxide, optionally in the presence of oxygen (see U.S. Pat. No. 5,679,875).

Similarly, fluorination and/or hydrofluorination steps are also common in the manufacturing processes of (hydro)fluoroalkenes. Such processes may be performed by contacting HF with one or more (hydro)haloalkenes or (hydro)haloalkanes, preferably in the presence of a catalyst.

Notwithstanding the above processes, catalytic reactions involving halocarbons have a number of problems in use, one of which is that industrial scale processes subject the catalysts to extreme temperatures and pressures, numerous regenerations and corrosive reagents. The skilled person will know that over the lifetime of an industrial catalyst the activity is steadily reduced and the catalyst must eventually be replaced in an expensive procedure.

There is therefore a need for catalysts with improved stability and comparable or improved activity and selectivity relative to existing catalysts.

In a first aspect, the present invention provides a catalyst comprising chromia and at least one additional metal or compound thereof, wherein the catalyst has a total pore volume of greater than 0.3 cm$^3$/g and the mean pore diameter is greater than or equal to 90 Å, wherein the total pore volume is measured by N$_2$ adsorption porosimetry and the mean pore diameter is measured by N$_2$ BET porosimetry, and wherein the at least one additional metal is selected from Li, Na, K, Ca, Mg, Cs, Sc, Al, Y, Ti, Zr, Hf, V, Nb, Ta, Cr, Mo, W, Mn, Re, Fe, Ru, Co, Rh, Ir, Ni, Pd, In, Pt, Cu, Ag, Au, Zn, La, Ce and mixtures thereof.

In a second aspect, there is provided a method for producing 2,3,3,3-tetafluoropropene (1234yf) from a saturated precursor in the presence of a catalyst as defined above.

This additional metal or compound thereof can also be referred to as a promoter. Preferably, the at least one additional metal is selected from Li, Na, K, Ca, Mg, Cs, Cr, Zr, Nb, Pd, Ta, Zn, V, Mo, Ni, Co, In, Fe, Cu and mixtures thereof, even more preferably the additional metal is zinc.

The skilled person would appreciate that in catalysis in general, catalytic activity is understood to be proportional to the available surface area of the catalyst. It is to be expected that increasing the opportunity for the reagents to interact with the surface of the catalyst will improve the rate of conversion.

However, in contrast to established teaching, the present inventors have surprisingly found that increasing the pore volume and average pore diameter, which may inherently reduce a catalyst's surface area, increases both the stability and the activity of the catalyst.

Without wishing to be bound by theory, it is believed that this is a result of the increased mass transfer through the catalyst and that this effect is more pronounced for C$_3$ compounds than C$_2$ compounds. Also without wishing to be bound by theory, it is believed that the wider pore diameters of the present invention allow the catalyst in use to assume more quickly an effective pore structure for producing (hydro)haloalkenes such as hydrofluoropropenes.

The pore structure of solid porous materials can be determined by several methods, one of the most commonly used is the adsorption and desorption of N$_2$, based on the BET theory (Brunauer, Emmett and Teller) of the adsorption of multilayers of condensed gases onto solid surfaces, and the evaporation (desorption) of the adsorbed gas during desorption. Nitrogen is a common adsorbate for probing the micro and mesoporous regions. From the adsorption and desorption isotherms, the following can be calculated: BET surface area from the adsorption of a monolayer of N$_2$, total pore volume taken from the amount of nitrogen adsorbed at P/P$^O$=0.99 and average pore diameters can be determined using different calculations either based on the BET theory or that of BJH (Barrett, Joyner and Halenda), either from the adsorption or desorption data.

Preferably, the total pore volume of the catalyst is equal to or greater than 0.35 cm$^3$/g or 0.4 cm$^3$/g, such as 0.45 cm$^3$/g, 0.5 cm$^3$/g, 0.55 cm$^3$/g or even 0.6 cm$^3$/g when measured by N$_2$ adsorption porosimetry.

Preferably, the average pore width of the catalyst is greater than or equal to 100 Å, e.g. greater than or equal to 110 Å or greater than or equal to 120 Å when measured by N$_2$ BET adsorption porosimetry.

Preferably, the average pore width of the catalyst is greater than or equal to 130 Å, e.g. greater than or equal to 140 Å, greater than or equal to 150 Å or greater than or equal to 170 Å when measured by N$_2$ BJH adsorption porosimetry.

Preferably, the average pore width of the catalyst is greater than or equal to 90 Å, e.g. greater than or equal to 100 Å, greater than or equal to 110 Å or greater than or equal to 120 Å when measured by N$_2$ BJH desorption porosimetry.

Preferably, the catalyst is provided in the form of a pellet or pellets comprising a plurality of catalyst particles. Such catalyst particles may be pressed together, for example under load, to form the pellets.

The pellets may comprise one or more further materials. For example, the pellets may include graphite, preferably in an amount of from about 0.5 wt % to about 10 wt %, e.g. from about 1 wt % to about 5 wt %.

Preferably, the pellets have a longest dimension from about 1 mm to about 100 mm. In some embodiments, the pellets may have a longest dimension of about 1 mm to about 10 mm, for example from about 3 mm to about 5 mm.

Preferably, the catalyst comprises at least 80 wt % (for example at least 85 wt %, at least 90 wt %, at least 92 wt %, at least 93 wt %, at least 94 wt %, at least 95 wt % or at least 96 wt %) chromia.

Advantageously, the catalyst may be a zinc/chromia catalyst. By the term "zinc/chromia catalyst" we mean that the metal oxide catalyst comprises chromium or a compound of chromium and zinc or a compound of zinc.

The total amount of the zinc or a compound of zinc present in the zinc/chromia catalysts of the invention is typically from about 0.01% to about 25%, preferably 0.1% to about 25%, conveniently 0.01% to 6% of the catalyst; and in some embodiments preferably 0.5% by weight to about 25% by weight of the catalyst, preferably from about 1 to 10% by weight of the catalyst, more preferably from about 2 to 8% by weight of the catalyst, for example about 4 to 6% by weight of the catalyst.

In further preferred embodiments, the additional metal compound may comprise indium (e.g. in the form $In_2O_3$) and/or zirconium (e.g. in the form $ZrO_2$).

Additional metals or compounds thereof are typically present from about 0.01% to about 25%, preferably 0.1% to about 25%, conveniently 0.01% to 6% by weight of the catalyst; and in some embodiments preferably 0.5% by weight to about 25% by weight of the catalyst, preferably from about 1 to 10% by weight of the catalyst, more preferably from about 2 to 8% by weight of the catalyst, for example about 4 to 6% by weight of the catalyst In other embodiments, the catalyst may be an alumina catalyst with one or more promoters selected from platinum, iron, chromium and zinc. The total amount of promoter is typically from about 0.1 to about 60% by weight of the catalyst, preferably from about 0.5 to about 50% by weight of the catalyst, such as 0.5% by weight to about 25% by weight of the catalyst, or from about 1 to 10% by weight of the catalyst.

In such embodiments it is preferred that the catalyst comprises at least 80 wt % (for example at least 85 wt %, at least 90 wt %, at least 92 wt %, at least 93 wt %, at least 94 wt %, at least 95 wt % or at least 96 wt %) chromia.

In some embodiments, the catalyst may be in fluorinated form. For example, the catalyst may have been fluorinated by treatment with HF at elevated temperature.

Advantageously, the catalysts of the present invention are unused, i.e. new. By 'unused' we mean that the catalyst possesses the total pore volume and average pore diameter, as specified above, before it has been contacted with any reagents or put under any pre-reaction conditions and/or the catalyst has not previously been used for catalysing a reaction or regenerated.

The present invention also provides a method of preparing a catalyst, said method comprising the steps of:
  a) preparing a metal salt solution and a hydroxide solution;
  b) combining the solutions at a pH of greater than 7.5 in order to precipitate the metal hydroxide(s);
  c) drying the precipitated metal hydroxides;
  d) calcining the metal hydroxide(s) to form the metal oxide(s).

Preferably, the metal salt comprises a nitrate salt such as a hydroxide nitrate salt. In preferred embodiments, the metal salt comprises chromium, and may comprise a chromium nitrate salt such as $Cr(OH)(NO_3)_2$. The hydroxide solution may comprise ammonium hydroxide ($NH_4OH$). Advantageously, step b) is carried out at a pH of greater than 8. Preferably, step b) is carried out at a pH of greater than or equal to 8.1, 8.2, 8.3; 8.4 or 8.5.

In some embodiments, the metal salt solution is provided at a concentration of from about 1 mol/l to about 10 mol/l, for example from about 2 mol/l to about 8 mol/l, e.g. from about 3 mol/l to about 7 mol/l or from about 4 mol/l to about 6 mol/l.

In some embodiments, the hydroxide solution is provided at a concentration of from 1 mol/l to about 10 mol/l, for example from about 2 mol/l to about 8 mol/l, e.g. from about 3 mol/l to about 7 mol/l or from about 4 mol/l to about 6 mol/l.

Preferably, step (b) is performed by combining the solutions in a body of solvent, such as water. Alternative solvents may include alcohols, glycols, water mixtures and other polar solvents.

Preferably, step b) is carried out at a substantially constant temperature, such as from 0 to 50° C., preferably from 10 to 30° C.

Preferably, step (b) is performed while agitating the combined solutions. Such agitation may be provided by known suitable means such as impellers, jet mixer, recirculation pumps and the like.

The precipitate formed during step (b) preferably comprises particles having average longest dimensions of from about 5 μm to about 20 μm, e.g. from about 7 μm to about 15 μm or from about 8 μm to about 13 μm, for example around 10 μm. Such dimensions are according to measurement by focussed beam reflectance measurement.

Preferably, step (c) includes removing liquid from the slurry of metal hydroxide precipitate(s) to produce a wet cake, for example by filtration or centrifugal action. Such filtration may include the application of a pressure differential across the or a filtration membrane. The cake may be washed prior to any drying or calcining, preferably by exposure to water (e.g. deionised water) or aqueous alkali (such as ammonium hydroxide).

Preferably step (c) includes removing liquid, e.g. residual liquid, from the wet metal hydroxide(s) cake by exposing it to elevated temperature. Such elevated temperature may be, for example, between 50° C. and 200° C. and more preferably may be between 80° C. and 150° C., e.g. around 90° C. to around 120° C. The precipitate is preferably exposed to the elevated temperature for at least 15 mins, e.g. at least 30 mins or at least 1 hr. In certain embodiments, the precipitate may be subject to elevated temperature for over 6 hr or over 12 hr.

It is also preferred that step (d) includes a step of calcining the metal hydroxide, preferably after liquid removal and/or drying. Such a calcining step may include heating the metal hydroxides to a temperature between around 200° C. and around 550° C., for example between around 250° C. and around 500° C., e.g. around 300° C. to around 400° C. Such a calcining step may have a duration of from around 5 mins to around 12 hrs. It is particularly preferred to perform the calcination for a sufficient period to produce a catalyst having a TGA loss on ignition (LOI) at 400° C. of less than around 15%, for example less than around 12% or less than around 10%, for example around 8%, when heated to 400° C.

The method preferably comprises combining the calcined metal oxide with graphite to provide a catalyst composition comprising around 0.1 wt % to around 10 wt % graphite. In preferred embodiments, the composition so formed may comprise around 0.5 wt % to around 5 wt % graphite. It is most preferred that the composition so formed comprises around 1 wt % to around 3 wt % graphite.

In preferred embodiments, the metal oxide and/or catalyst composition may be pressed to form catalyst pellets. The pressing may take place under a load of around 1 to 10 tonnes, e.g. around 5 tonnes. The pellets so formed may have a longest dimension from about 1 mm to about 100 mm. In some embodiments, the pellets may have a longest dimension of about 1 mm to about 10 mm, for example from about 3 mm to about 5 mm.

In embodiment further aspect of the invention, there is provided a process for fluorinating a $C_{2-3}$ hydrohalocarbon species, comprising contacting the species with a catalyst according to the invention. This is typically carried out in the presence of HF. For the avoidance of doubt, the term $C_{2-3}$ hydrohalocarbon includes saturated or unsaturated compounds with a two or three carbon chain and containing one or more atoms of hydrogen and a halogen (F, Cl, Br, I). In preferred embodiments, the hydrohalocarbon species comprises a $C_3$ hydrohalocarbon species.

An example of such a process comprises contacting trichloroethylene with the catalyst in the presence of HF to produce 1,1,1,2-tetrafluoroethane (134a), the conversion of 1,1,1,2,3-pentachloropropane (240db) to 2-chloro-3,3,3-trifluoropropene (1233xf), the conversion of 1233xf to 2,3,3,3-tetrafluoropropene (1234yf) and/or 1,1,1,2,2-pentfluoropropane (245cb), the conversion of 1,1,1,3-tetrachloropropane (250fb) to 3,3,3-trifluoropropene (1243zf), or the conversion of 2,3-dichloro-1,1,1-trifluoropropane (243db) to 1233xf and/or 1234yf.

In another aspect of the invention, there is provided a process for dehydrohalogenating a $C_{2-3}$ hydrohalocarbon species (preferably a $C_3$ hydrohalocarbon species), comprising contacting the species with a catalyst, such as contacting a hydro(halo)fluoropropane with the catalyst to produce a fluoropropene, preferably a tetrafluoropropene (1234) such as 1234ze ((E) or (Z)) or 1234yf. Advantageously, this may include the conversion of 245cb and/or 1,1,1,2,3-pentafluoropropane (245eb) to 2,3,3,3-tetrafluoropropene (1234yf) and/or 1,3,3,3-tetrafluoropropene (1234ze), the conversion of 1,1,1,3,3-pentafluoropropane (245fa) to 1234ze or the conversion of 1-chloro-1,3,3,3-tetrafluoropropane to 1-chloro-3,3,3-trifluoropropene (1233zd) or 1234ze.

In a further aspect of the invention, there is provided a process for eliminating HF or from a saturated $C_{2-3}$ hydrohalocarbon species (preferably a $C_3$ hydrohalocarbon species), comprising contacting the species with a catalyst according to the invention.

In another aspect of the invention, there is provided a process for adding HF to an unsaturated $C_{2-3}$ hydrohalocarbon species (preferably a $C_3$ hydrohalocarbon species), comprising contacting the species with a catalyst according to the invention.

The claimed processes may be conducted in the liquid or the vapour phase but are preferably conducted in the vapour phase. The process may be carried out at atmospheric, sub- or super atmospheric pressure, typically at from 0 to about 30 bara, preferably from about 1 to about 20 bara, such as 15 bara.

Typically, the vapour phase process of the invention is carried out a temperature of from about 100° C. to about 500° C. (e.g. from about 150° C. to about 500° C. or about 100 to about 450° C.). Preferably, the process is conducted at a temperature of from about 150° C. to about 450° C., such as from about 150° C. to about 400° C., e.g. from about 175° C. to about 300° C. Lower temperatures may also be used in the conversion of 250fb to 1243zf, such as from about 150° C. to about 350° C., e.g. from about 150° C. to about 300° C. or from about 150° C. to about 250° C.

The processes typically employ a molar ratio of HF:organics of from about 1:1 to about 100:1, such as from about 3:1 to about 50:1, e.g. from about 4:1 to about 30:1 or about 5:1 or 6:1 to about 20:1 or 30:1.

The reaction time for the process generally is from about 1 second to about 100 hours, preferably from about 10 seconds to about 50 hours, such as from about 1 minute to about 10 or 20 hours. In a continuous process, typical contact times of the catalyst with the reagents are from about 1 to about 1000 seconds, such from about 1 to about 500 seconds or about 1 to about 300 seconds or about 1 to about 50, 100 or 200 seconds.

The present invention will now be illustrated by the following non-limiting Examples, illustrated by the following drawings.

EXAMPLES

Figure 1:
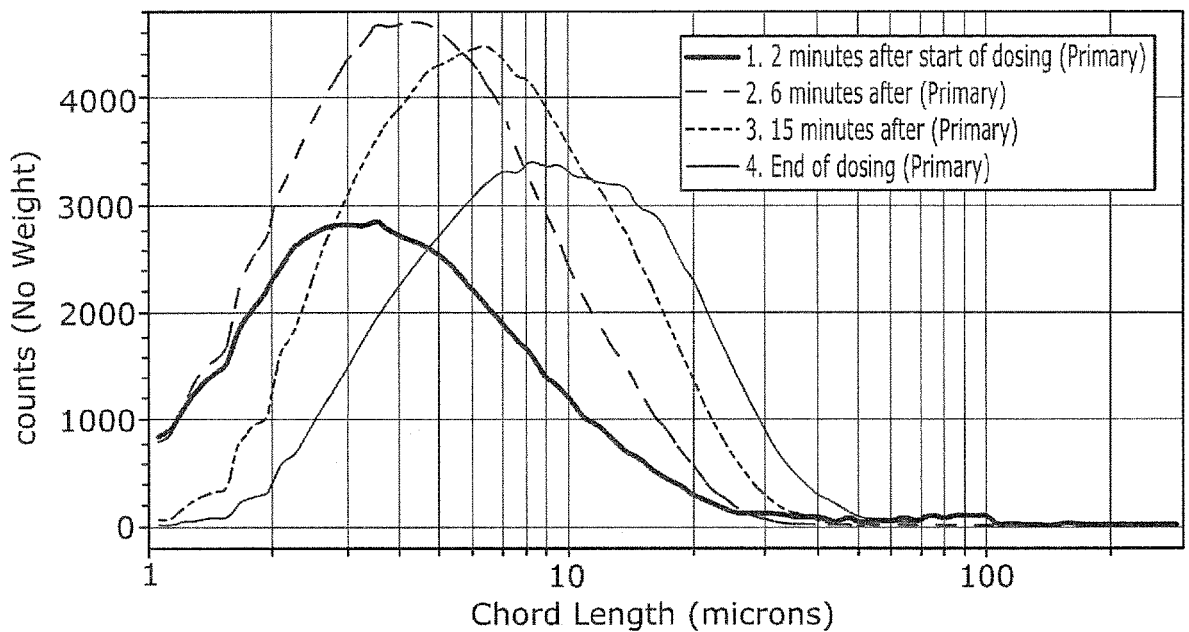
FIG. 1 shows a plot of the particle size distribution at temporal points during the reaction of Comparative Example 8, unweighted to emphasise smaller particles.

Catalysts of examples 1 to 7 were produced by the following method:

500 mL deionised water heel was added to a 1.7 L jacketed glass vessel, fitted with an overflow, overhead stirrer, pH probe and thermocouple and cooled to 15° C. The stirrer was actuated at 500 rpm, save for in example 5, where it was turned at 250 rpm.

$Zn(NO_3)_2.6H_2O$ (19.03 g) was dissolved into a solution of $Cr(NO_3)_2(OH)_{(aq)}$ (500 g) in a 600 mL beaker. In another beaker, 500 g 17% $NH_4OH$ solution was provided.

The metal and ammonia solutions were pumped into the chilled water at 5 ml/min. Precipitation of a green/blue solid occurs immediately. The pH of the mixture was monitored and the reactant flow rates adjusted to maintain the target pH for each example as shown in Table 1, below. The reaction was run until all of the metal solution was added.

The slurry was filtered under vacuum until a filter cake formed then washed four times with de-ionised water ("a" examples) or dilute aqueous ammonia solution ("b" examples).

The filter cake was then dried at 105° C. overnight in a standard oven, followed by calcining under flowing nitrogen (200 ml/min) at 300° C. for 12 hours to produce 6.5% $ZnO/Cr_2O_3$, the heating rate on the chamber furnace being set to 2° C./min. The percentage mass loss was on calcination was noted.

2 wt % graphite was blended with the cooled, calcined catalyst precursor in a waring blender, and the resultant catalyst mixture was sieved to <250 μm. The sieved mixture was formed into pellets under a load of 5 tonne in a 32 mm pellet die, 3 g per pellet.

The pellets were then ground to mesh size 0.5-1.4 mm for catalyst testing. Surface area, pore volumes and sizes were measured by $N_2$ adsorption/desorption porosimetry. Zn content was measured by X-ray fluorescence spectroscopy. The results are shown in Table 1, alongside results for Comparative Example 1, a chromia catalyst having a specified surface area of 160 to 200 $m^2/g$ and pore volume of greater than 0.22 $cm^3/g$.

size in the range 0.5-1.4 mm. Initially the nitrogen flow (60 ml/min) was directed to the reactor inlet and the catalysts dried at 250° C. for 1 hour.

Following the catalyst drying operation HF vapour was fed to each reactor at a flow of 30 ml/min, diluted with nitrogen (60 ml/min), and passed over the catalysts at 250° C. for approximately 30 minutes until HF was observed in the reactor off gases. At this point the nitrogen flows (reduced to 30 ml/min) were redirected to the reactor exits. The catalysts were then exposed to the $HF:N_2$ (30:5-ml/min) stream for a further hour at 250° C. before the temperatures were ramped to 450° C. at 40° C. per hour. These temperatures were held for ten hours.

The reactors were initially cooled to 350° C. and trichloroethylene was fed over the catalysts by sparging nitrogen (8 ml/min) through liquid trichloroethylene at 10° C. This gave a 0.5 ml/min flow of trichloroethylene gas. The catalysts were allowed to equilibrate in the $HF:trichloroethylene:N_2$ (30:0.5:10-ml/min) gas stream for about 2 hours before the reactor temperatures were reduced to 300° C. The catalysts were again allowed to equilibrate for about 1 hour before the production of 133a and 134a from each was measured. The temperatures and yields across the reactors were monitored.

The organic feed was then turned off and with 30 ml/min HF flowing over the catalyst the reactor temperatures were ramped to 490° C. at 40° C./hr this was held for ten hours and cooled to 350° C. Trichloroethylene was then provided as above. This process was repeated for a stress temperature of 514° C. and, for some examples 522° C.

The activity and stability results are presented as a comparison to the results for Comparative Example 1, a commercial catalyst tested under the same conditions.

Activity is determined according to the calculation $$Activity = 50 - (S2 - RT)$$

TABLE 1

| Example | Actual pH | Water Heel/g | Stirrer speed/rpm | Temp/° C. | Slurry Wash Sol$^n$ | BET SA ($m^2$/g) | Pore Volume ($cm^3$/g) @ 0.99P/P° | BET Ads Average pore width (Å) | BJH Ads Average pore width (Å) | BJH Des Average pore width (Å) |
|---|---|---|---|---|---|---|---|---|---|---|
| CE1 | | | | | | 180 | 0.282 | 63 | 107 | 65 |
| CE2a | 7.2-7.3 | 500 | 500 | 15-17 | DI $H_2O$ | 171 | 0.259 | 60 | 112 | 63 |
| CE2b | | | | | $NH_4OH$ | 125 | 0.221 | 71 | 124 | 72 |
| 3a | 7.5-8.1 | 500 | 500 | 15-16 | DI $H_2O$ | 125 | 0.327 | 105 | 147 | 102 |
| 3b | | | | | $NH_4OH$ | 127 | 0.382 | 121 | 169 | 116 |
| 4 | 8.3 | 500 | 500 | 15-16 | DI $H_2O$ | 129 | 0.442 | 137 | 184 | 129 |
| 5a | 8.3-8.4 | 500 | 500 | 17-18 | DI $H_2O$ | 111 | 0.449 | 162 | 190 | 143 |
| 5b | | | | | $NH_4OH$ | 111 | 0.464 | 167 | 195 | 147 |
| 6a | 8.3-8.4 | 500 | 500 | 15-16 | DI $H_2O$ | 172 | 0.506 | 118 | 192 | 127 |
| 6b | | | | | $NH_4OH$ | 138 | 0.447 | 129 | 189 | 131 |
| 7a | 8.2-8.4 | 500 | 500 | 15-17 | DI $H_2O$ | 132 | 0.512 | 155 | 198 | 148 |
| 7b | | | | | $NH_4OH$ | 151 | 0.508 | 135 | 191 | 138 |

$N_2$ Porosimetry (200-500 μm, outgassed 300° C., 3 h, $N_2$)

The data clearly shows that a significant raising of the pore volume of a precipitated catalyst is provided when the pH of precipitation is raised.

The pelleted catalysts were tested for their efficacy in converting trichloroethylene to 134a. An atmospheric pressure screening rig was equipped with four reactor tubes, each with independent HF, organic and nitrogen feeds. The organic feed system was charged with trichloroethylene. Each reactor was charged with 2 g of catalyst with a particle where S2 is the predicted reaction temperature to obtain 10% 134a yield at Stress Temperature 2 and where RT is 287.5° C.

Stability is determined according to the calculation $$Stability = 50 - (S3 - RT)$$

where S3 is the predicted reaction temperature to obtain 10% 134a yield at Stress Temperature 3 and where RT is 287.5° C.

The results are shown in Table 2, below.

TABLE 2

| Example | Precipitation pH | Predicted Reaction Temp to Obtain 10% 134a Yield | | | | Activity | Stability |
|---|---|---|---|---|---|---|---|
| | | Stress 1 450° C. | Stress 2 490° C. | Stress 3 514° C. | Stress 4 522° C. | | |
| CE 1 | | 288.90 | 287.50 | 295.50 | 318.90 | 50 | 42 |
| CE2a | 7.2-7.3 | 296.00 | 297.04 | 308.61 | — | 40.5 | 28.9 |
| CE2b | | 307.64 | 292.58 | 301.11 | — | 44.9 | 36.4 |
| 3a | 7.5-8.1 | 287.22 | 284.37 | 291.35 | — | 53.1 | 46.2 |
| 3b | | — | 279.71 | 281.90 | — | 57.8 | 55.6 |
| 4 | 8.3 | 284.70 | 286.04 | 284.79 | 304.00 | 51.5 | 52.7 |
| 5a | 8.3-8.4 | 288.46 | 286.80 | 290.93 | 308.82 | 50.7 | 46.6 |
| 5b | | 286.78 | 284.96 | 289.00 | 308.18 | 52.5 | 48.5 |
| 6a | 8.3-8.4 | 282.16 | 279.32 | 283.17 | 301.29 | 58.2 | 54.3 |
| 6b | | 281.68 | 285.05 | 288.90 | 306.29 | 52.5 | 48.6 |
| 7a | 8.2-8.4 | 281.48 | 282.46 | 288.26 | 303.83 | 55.0 | 49.2 |
| 7b | | 282.35 | 278.32 | 282.84 | 297.90 | 59.2 | 54.7 |

The results show a clear correlation between increased pore volume and width and increased stability and activity over prior art catalysts. This activity appears to be sustained even where there is a decrease in surface area compared to the commercial catalyst.

Comparative Examples 8, 9 and 10 and Example 11

Catalysts were prepared substantially according to the method of Examples 1 to 8, adapted as described below with reference to Table 3.

A Mettler Toledo Optimax automated laboratory reactor was fitted with Focussed Beam Reflective Measurement (FBRM) G400 14 mm probe with overhead stirring and charged with 500 ml a deionised water heel.

The metal solution was pumped to the reactor at 5 ml/min. 17% Ammonium hydroxide solution was also added at 5 ml/min. The pH was closely monitored and the flow rates of the reactants altered to maintain the target pH. The reaction was run until 300 g of the metal solution was added. The particle size of the precipitate was monitored during the reaction using the FBRM G400 probe.

TABLE 3

| Example | Metal solution | Target pH |
|---|---|---|
| CE8 | 300 g Chromium hydroxide nitrate (~10% Cr) | pH 7 |
| CE9 | 300 g Chromium hydroxide nitrate (~10% Cr) | pH 8.5 |
| CE10 | 300 g Chromium hydroxide nitrate (~10% Cr) + 11.4 g $Zn(NO_3)_2 \cdot 6H_2O$ | pH 7 |
| 11 | 300 g Chromium hydroxide nitrate (~10% Cr) + 11.4 g $Zn(NO_3)_2 \cdot 6H_2O$ | pH 8.5 |

The resulting slurries were vacuum filtered and washed three times with de-ionised water. The filter cake was dried at 110° C. then, calcined under flowing nitrogen (200 ml/min) at 300° C. for 12 hours to produce $Cr_2O_3$ and 6.5% $ZnO/Cr_2O_3$. This was milled and mixed with 2% graphite before being pelleted at 5 tonne.

Comparative Example 8

Figure 2:
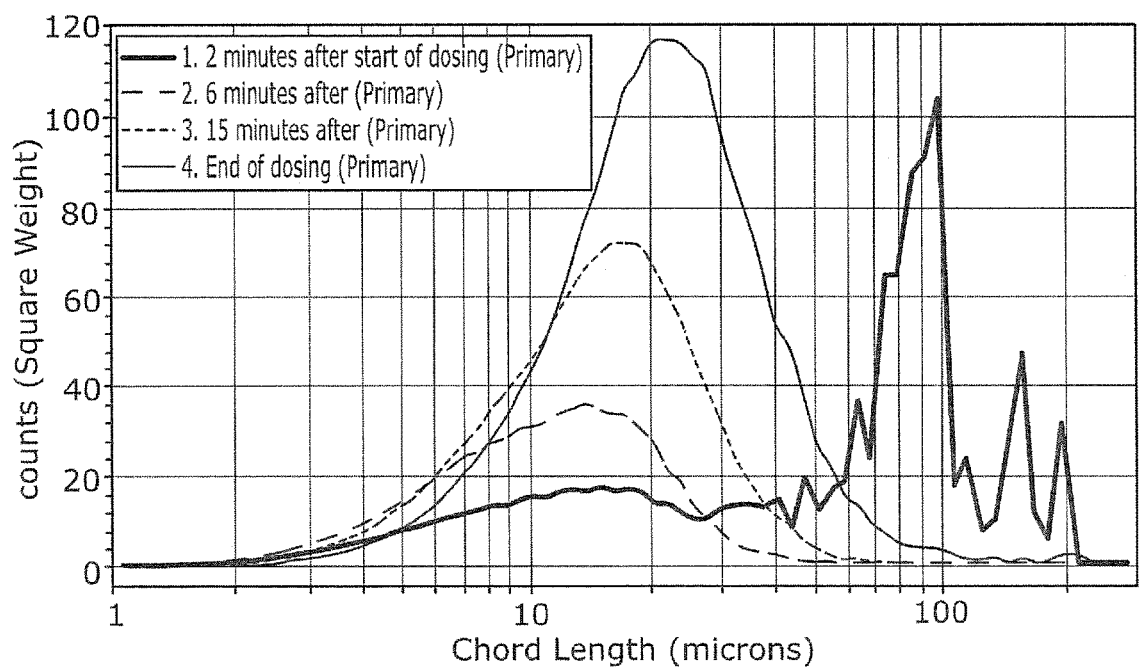
FIG. 2 shows a plot of the particle size distribution at temporal points during the reaction of Comparative Example 8, weighted to emphasise larger particles.

FIGS. 1 and 2 and table 4 show the measured particle size distribution 2, 6 and 15 minutes after the start of dosing and once dosing is complete. 2 minutes after the start there are mostly very small particles, but also a few large particles present. These large particles are not present 6 minutes after the start of dosing, by which time the small particle population is at its greatest. Thereafter, the distribution shows a gradual shift to large size.

TABLE 4

| Statistic | 2 min. | 6 min. | 15 min. | End |
|---|---|---|---|---|
| Median No Wt | 3.7 | 4.3 | 6.2 | 8.7 |
| Mean Sq Wt | 67.8 | 12.6 | 16.6 | 24.4 |
| Counts <5 μm | 45949 | 66179 | 42031 | 21046 |
| Counts 5-8 μm | 12838 | 25269 | 27048 | 19349 |
| Counts 8-25 μm | 10920 | 22241 | 37550 | 42532 |
| Counts 25-300 μm | 1493 | 357 | 1576 | 5377 |

Comparative Example 9

Figure 3:
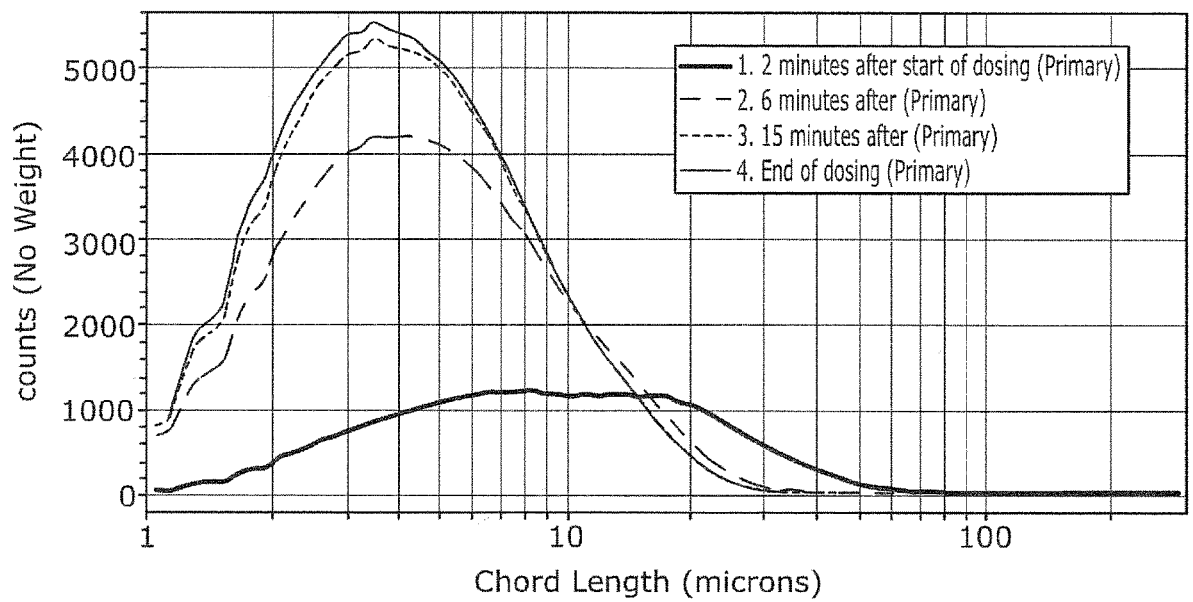
FIG. 3 shows a plot of the particle size distribution at temporal points during the reaction of Comparative Example 9, unweighted to emphasise smaller particles.
Figure 4:
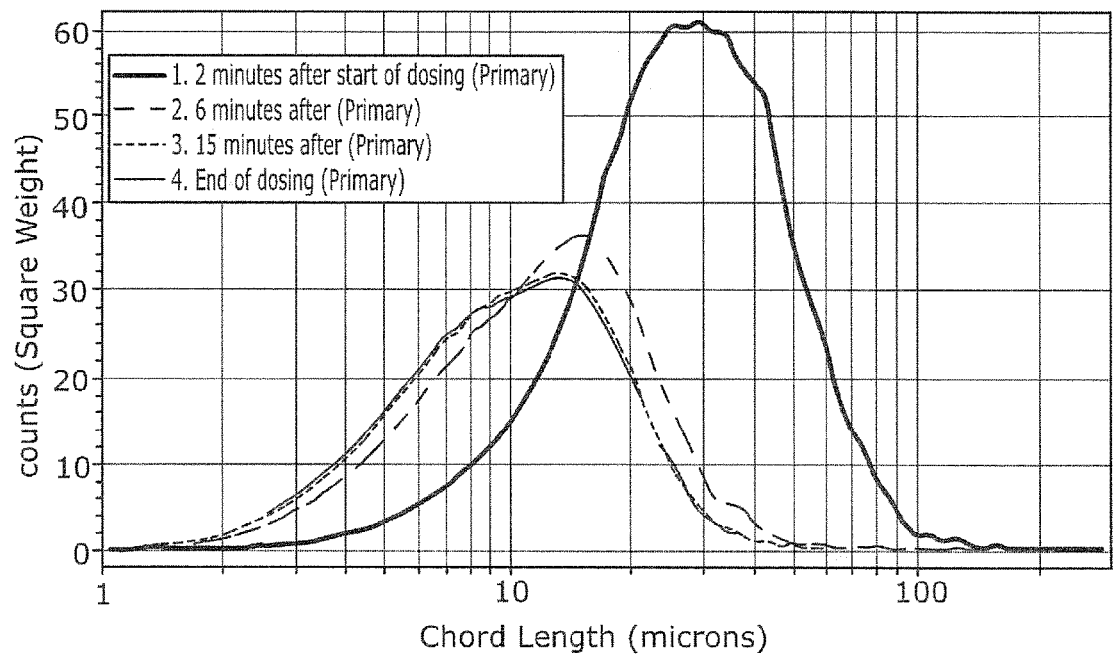
FIG. 4 shows a plot of the particle size distribution at temporal points during the reaction of Comparative Example 9, weighted to emphasise larger particles.

FIGS. 3 and 4 and table 5 show the measured particle size distribution 2, 6 and 15 minutes after the start of dosing and once dosing is complete. 2 minutes after the start there are mostly large particles present. But by 6 minutes, the number of large particles has reduced, and the number of small particles has increased significantly. The particle system shows very little change for the final 15 minutes of dosing.

TABLE 5

| Statistic | 2 min. | 6 min. | 15 min. | End |
|---|---|---|---|---|
| Median No Wt | 8.6 | 4.3 | 4.0 | 3.9 |
| Mean Sq Wt | 30.1 | 13.4 | 11.8 | 11.5 |
| Counts <5 | 10732 | 60239 | 77458 | 81366 |
| Counts 5-8 | 7135 | 22430 | 26103 | 26522 |
| Counts 8-25 | 16259 | 21560 | 20603 | 20341 |
| Counts 25-300 | 3858 | 460 | 233 | 228 |

Comparative Example 10

Figure 5:
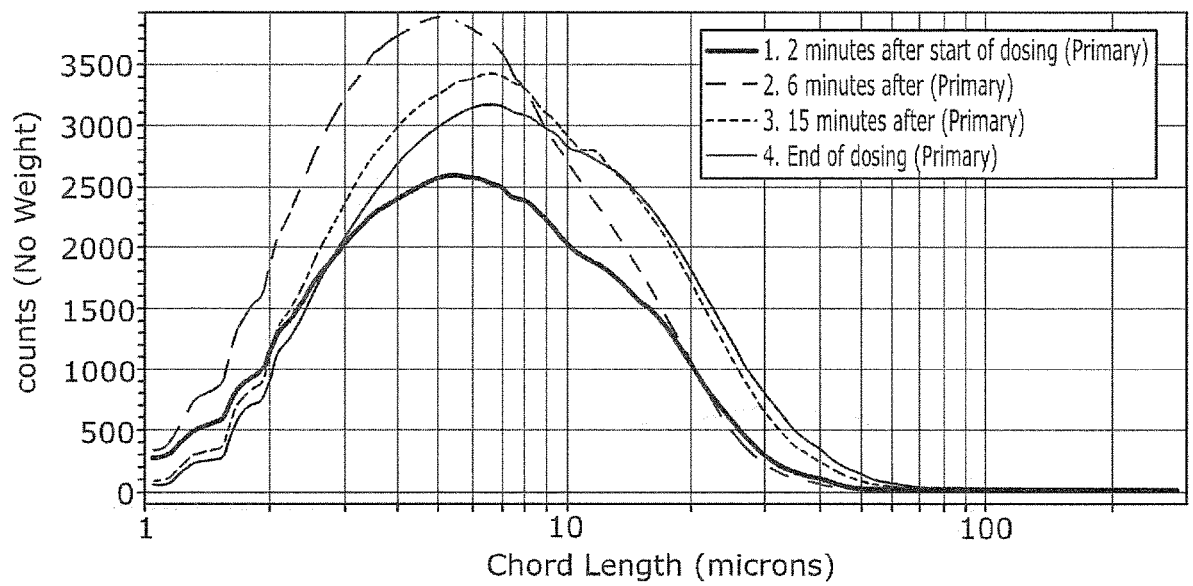
FIG. 5 shows a plot of the particle size distribution at temporal points during the reaction of Comparative Example 10, unweighted to emphasise smaller particles.
Figure 6:
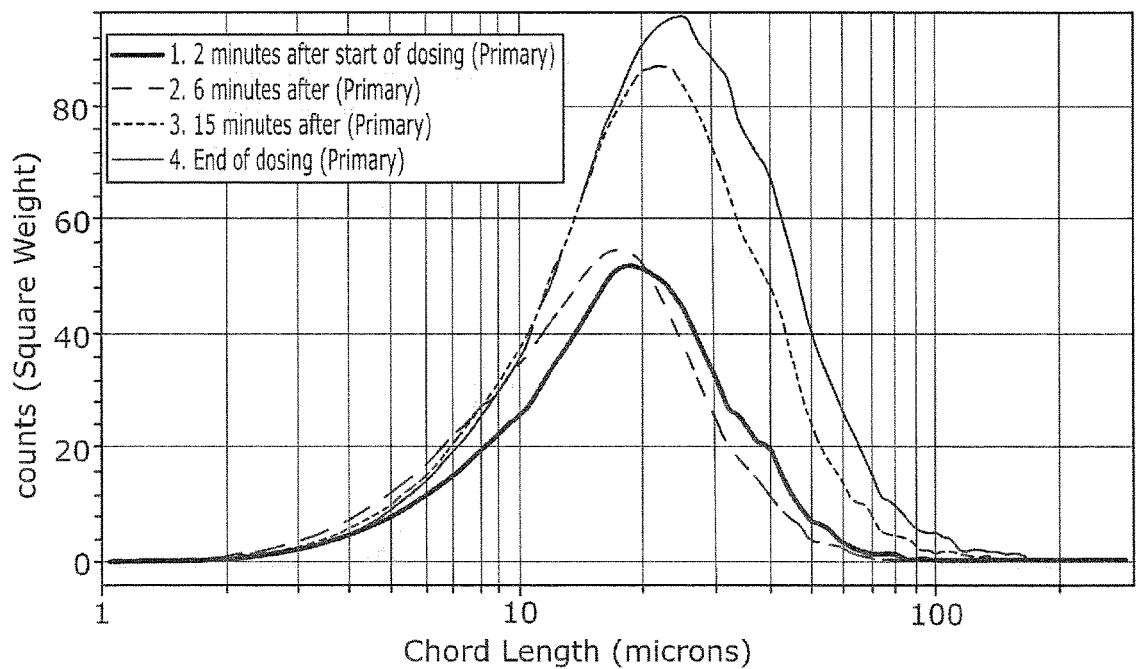
FIG. 6 shows a plot of the particle size distribution at temporal points during the reaction of Comparative Example 10, weighted to emphasise larger particles.

FIGS. 5 and 6 and table 6 show the measured particle size distribution 2, 6 and 15 minutes after the start of dosing and once dosing is complete. 2 minutes after the start there are mostly small particles present which increase in number as 6 minutes is reached. After that, the population of those small particles gradually decreases, and the number of larger particles increases.

TABLE 6

| Statistic | 2 min. | 6 min. | 15 min. | End |
|---|---|---|---|---|
| Median No Wt | 5.9 | 5.3 | 6.8 | 7.3 |
| Mean Sq Wt | 19.7 | 17.0 | 23.4 | 26.7 |
| Counts <5 μm | 29859 | 46790 | 32806 | 28764 |
| Counts 5-8 μm | 15510 | 22717 | 20755 | 19240 |
| Counts 8-25 μm | 23382 | 28384 | 35207 | 35337 |
| Counts 25-300 μm | 1798 | 1346 | 4113 | 5314 |

Example 11

Figure 7:
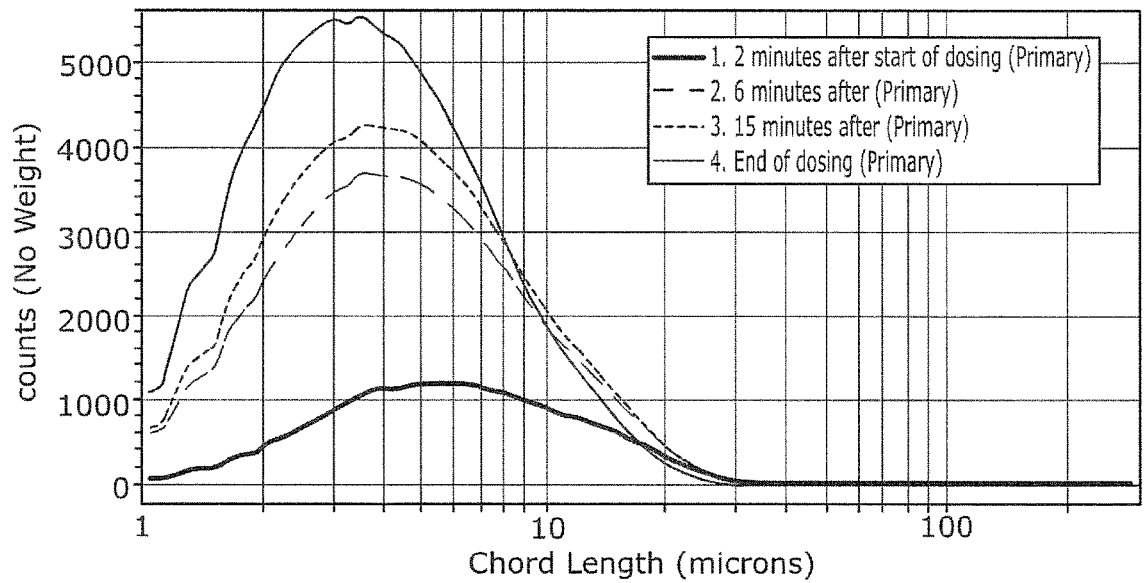
FIG. 7 shows a plot of the particle size distribution at temporal points during the reaction of Example 11, unweighted to emphasise smaller particles.
Figure 8:
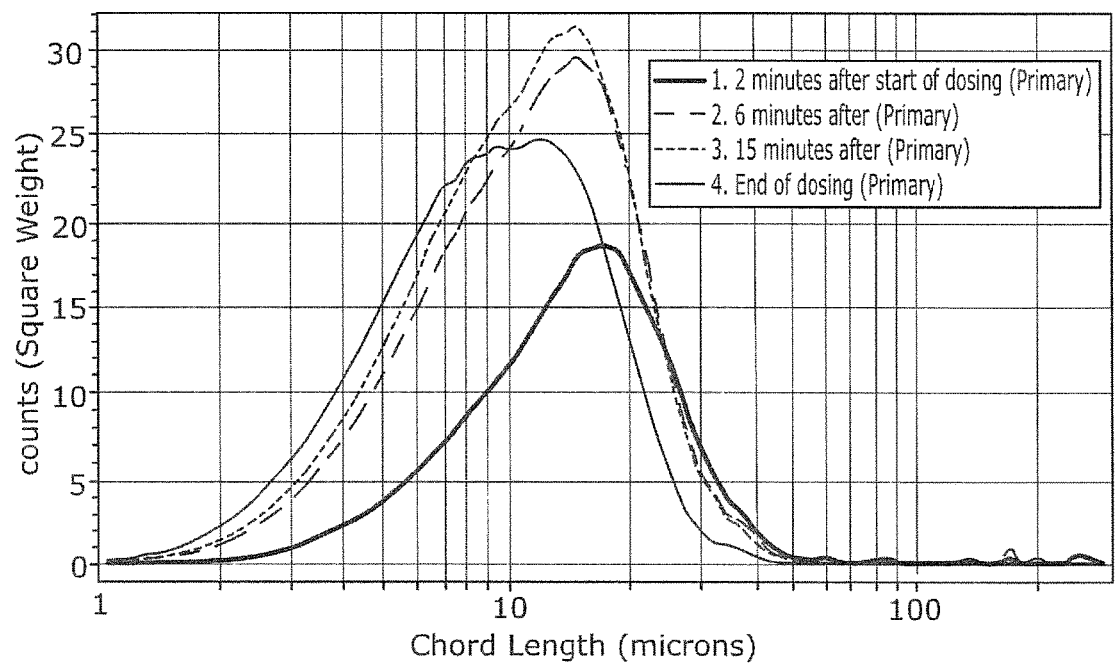
FIG. 8 shows a plot of the particle size distribution at temporal points during the reaction of Example 11, weighted to emphasise larger particles.

FIGS. 7 and 8 and table 7 show the measured particle size distribution 2, 6 and 15 minutes after the start of dosing and once dosing is complete. The distributions show that over the course of dosing, there is a gradual increase in the numbers of smaller particles. For the final 15 minutes of dosing, there is a decrease in the number of larger particles.

TABLE 7

| Statistic | 2 min. | 6 min. | 15 min. | End |
|---|---|---|---|---|
| Median No Wt | 5.7 | 4.3 | 4.1 | 3.6 |
| Mean Sq Wt | 16.8 | 13.2 | 12.4 | 10.4 |
| Counts <5 μm | 12933 | 52574 | 61877 | 87005 |
| Counts 5-8 μm | 7197 | 19203 | 21662 | 24208 |
| Counts 8-25 μm | 9559 | 17822 | 19193 | 16282 |
| Counts 25-300 μm | 352 | 297 | 284 | 112 |

Figure 9:
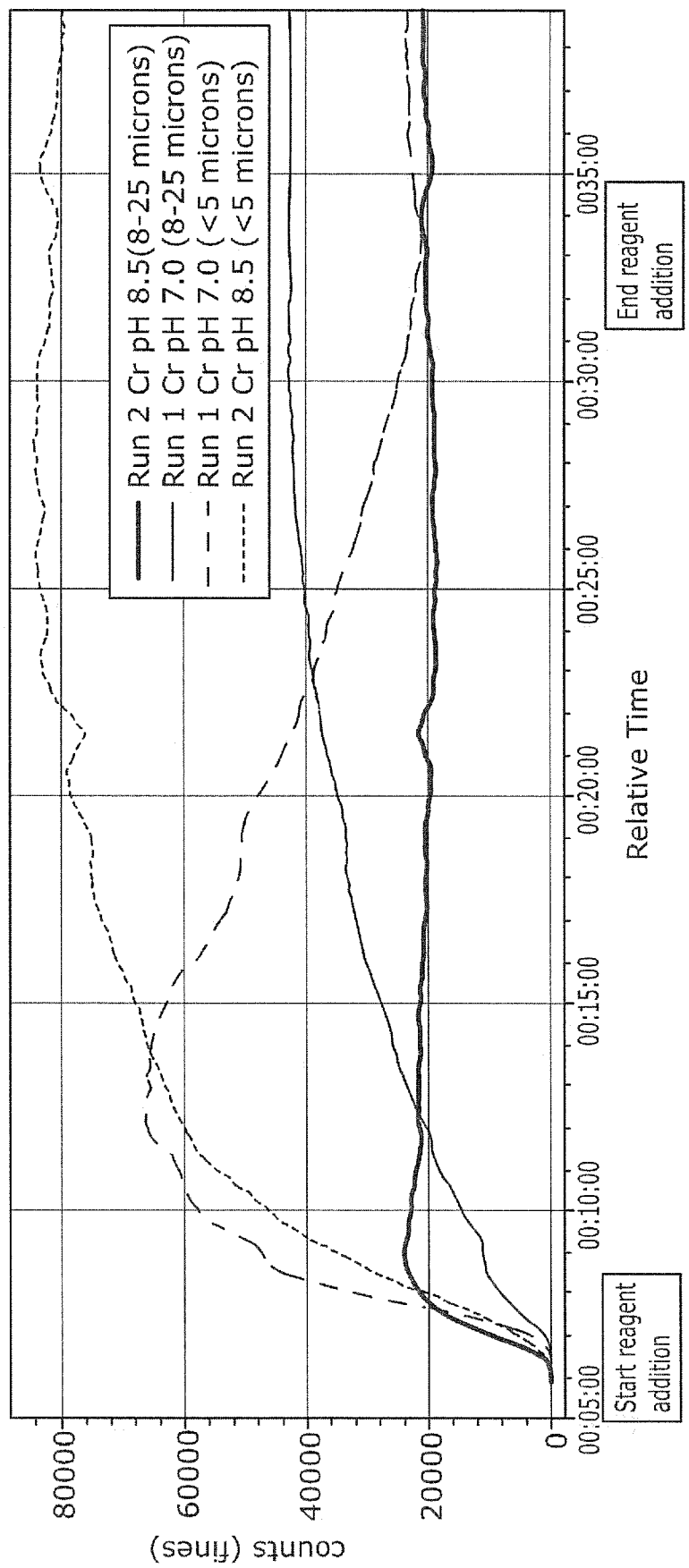
FIG. 9 shows a plot of the presence of fine particles during the reactions of Examples and Comparative Examples 8 to 11.

FIG. 9 shows the real time data collection for the fines count (both less than 5 μm and 8 μm to 25 μm) for Comparative Example 8 and 9. From this it was possible to see instantly the effect of any flow disturbances or pH fluctuations. It also demonstrates that leaving the final slurry to stir for an extended period had no effect on particle size or distribution.

Figure 10:
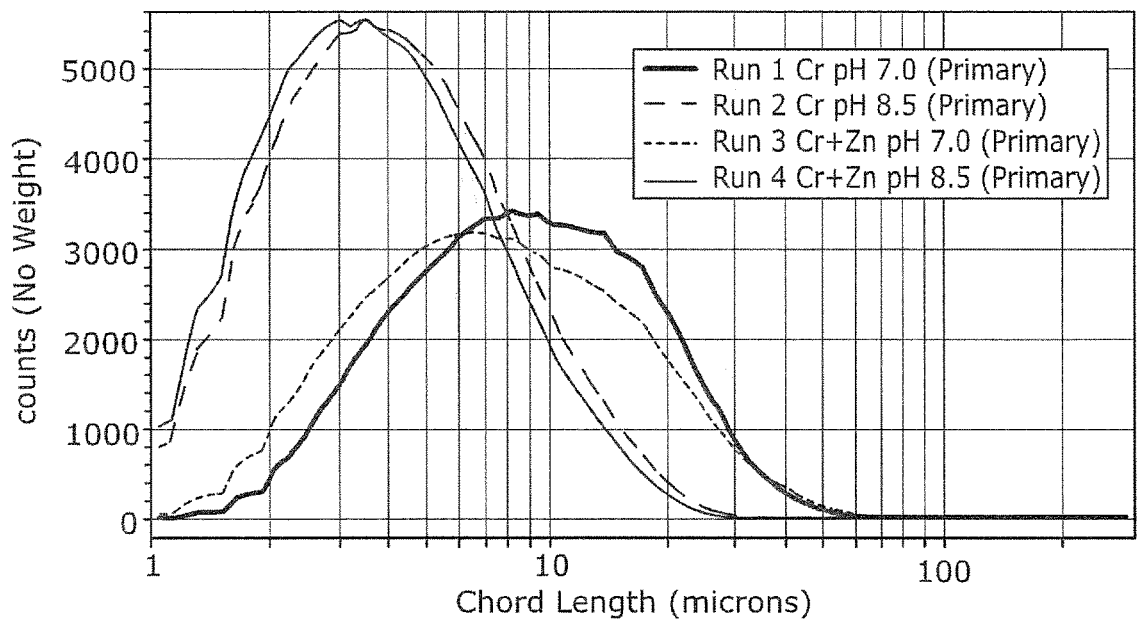
FIG. 10 shows a plot of the particle size distributions at completion of the reactions of Examples and Comparative Examples 8 to 11 unweighted to emphasise smaller particles.
Figure 11:
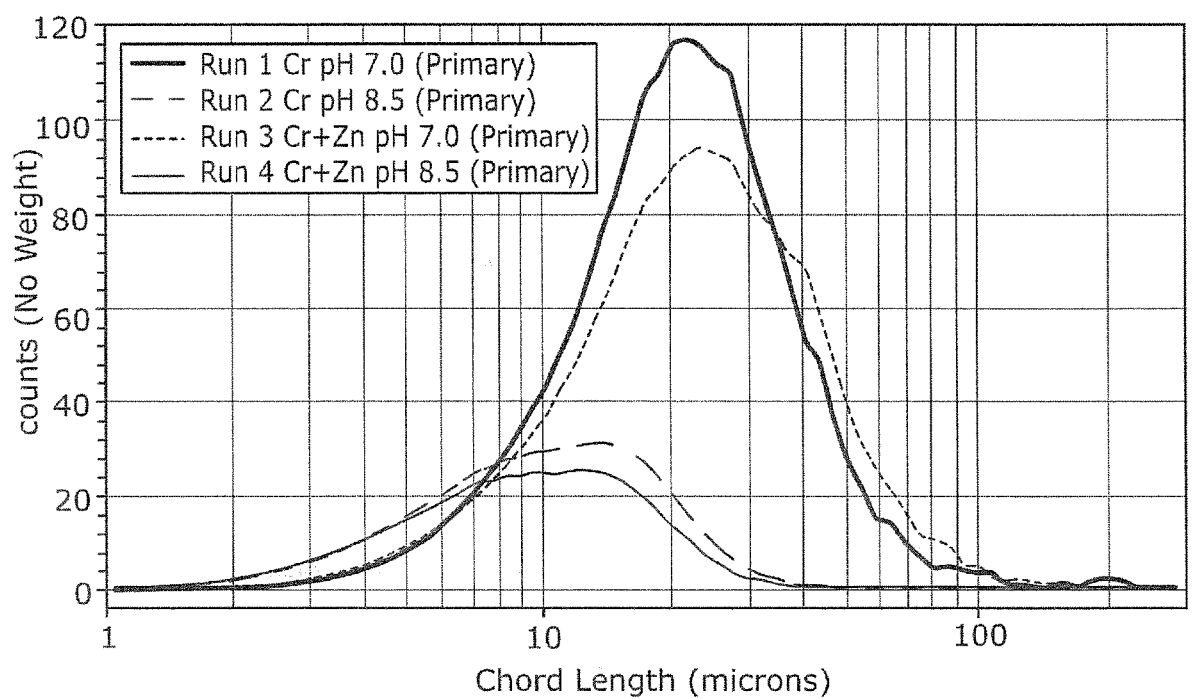
FIG. 11 shows a plot of the particle size distributions at completion of the reactions of Examples and Comparative Examples 8 to 11 weighted to emphasise larger particles.

A comparison of the final particle size distributions of the slurries is shown in FIGS. 10 and 11 and Table 8. The results clearly show that increasing the pH of precipitation has a significant effect on the particle population and size. Both runs at pH 8.5 have a smaller average size than those at pH 7.0, and more small particles. Changing the metal composition also has an effect—but much smaller in scale. Both runs with zinc show a slightly smaller average size compared to the chromium only counterparts.

The resulting dried, calcined and pelleted catalysts were tested by $N_2$ adsorption/desorption porosimetry to determine surface area, total pore volume and average pore diameter. The results are shown in Table 8, below.

TABLE 8

| Example | pH | Mean particle length (slurry) Microns | BET $m^2/g$ | Pore volume $cm^3/g$ @P/P °0.99 | BJH Ads Average pore diameter Å |
|---|---|---|---|---|---|
| CE8 | 7 | 24.5 | 243.75 | 0.21 | 51.2 |
| CE9 | 8.5 | 11.4 | 207.69 | 0.64 | 189.2 |
| CE10 | 7 | 26.5 | 241.00 | 0.45 | 100.1 |
| 11 | 8.5 | 10.5 | 200.98 | 0.72 | 206.7 |

It is clear that the catalysts of Comparative Examples, 8 and 10 (prepared at pH 7) had a larger particle size in the slurry and a larger BET surface area and a smaller pore diameter and volume. In contrast, the catalysts of Comparative Example 9 and Example 11 (prepared at pH 8.5) had a smaller particle size in the slurry which resulted in a smaller BET surface area and a larger pore diameter and volume.

The catalysts of Comparative Example 8, 9 and 10 and Example 11 were subjected to the same performance testing as Examples 1 to 7. The results are shown in Table 9 below.

TABLE 9

| | | | Predicted temp to Obtain 10% 134a Yield | | |
|---|---|---|---|---|---|
| Example | Activity | Stability | Stress 1 450° C. | Stress 2 490° C. | Stress 3 514° C. |
| CE8 | 42.4 | 34.33 | 285.03 | 295.10 | 303.17 |
| CE9 | 50.27 | 48.38 | 287.36 | 287.23 | 289.12 |
| CE10 | 45.89 | 46.93 | 295.66 | 291.61 | 290.57 |
| 11 | 59.08 | 46.27 | 274.38 | 278.42 | 291.23 |

These results show improved stability of the catalysts of Comparative Example 9 and Example 11 over the comparative Examples 8 and 10. This demonstrates that the favouring of larger pore sizes, larger pore volumes and/or smaller precipitated particle diameter upon precipitation over BET surface area provides for improved performance in the catalysts. These parameters may be controlled by controlling the pH of precipitation.

Preferences and options for a given aspect, feature or parameter of the invention should, unless the context indicates otherwise, be regarded as having been disclosed in combination with any and all preferences and options for all other aspects, features and parameters of the invention.

Examples and Comparative Examples 12 to 23

The catalyst of Comparative Example was made according to the following method. 20 500 mL deionised water heel was added to a 1.7 L jacketed glass vessel, fitted with an overflow, overhead stirrer, pH probe and thermocouple and cooled to 15° C. The stirrer was actuated at 500 rpm A solution of $Cr(NO_3)_2(OH)_{(aq)}$ (1036 g) was measured into a 2000 mL beaker. In another beaker, 599 g 17% $NH_4OH$ solution was provided.

The metal and ammonia solutions were pumped into the chilled water at 5 ml/min. Precipitation of a green/blue solid occurs immediately. The pH of the mixture was monitored and the reactant flow rates adjusted to maintain the target of pH 8.5. The reaction was run until all of the metal solution was added.

The chromium hydroxide slurry was divided into two portions and filtered separately under vacuum until a filter cake formed then each washed three times with de-ionised water (3×500 mL). The resulting filter cakes were combined, then divided into four. One portion of cake was then dried at 80° C. for 3-days in a standard oven to form the catalyst for Comparative Example 20. The remaining three were placed in separate beakers (600 ml) containing 200 mL deionised water with magnetic stirrer bars and mixed until the filter cake was re-slurried.

For Example 21, $MoCl_5$ (1.08 g) was added to 20 ml deionised water and the resulting solution added to one of the beakers containing chromium hydroxide slurry, and stirred at room temperature for 2 h.

For Example 22, $NiCl_2.6H_2O$ (1.53 g) was added to 20 ml deionised water and the resulting solution added to one of the beakers containing chromium hydroxide slurry, and stirred at room temperature for 2 h.

For Example 23, $NbCl_5$ (1.10 g) was added to 20 ml methanol and the resulting solution added to one of the beakers containing chromium hydroxide slurry, and stirred at room temperature for 2 h.

Each of the above slurries were then dried at 80° C. for 3-days in a standard oven, followed by calcining under flowing nitrogen (200 ml/min) at 300° C. for 12 hours to produce metal oxide/$Cr_2O_3$, (metal=Ni, Nb or Mo) the heating rate on the chamber furnace being set to 2° C./min. The percentage mass loss was on calcination was noted.

The reactor temperatures were ramped to 360° C. at 40° C. per hour. These temperatures were held for ten hours.

The reactors were cooled to 350° C. and 243db was fed over the catalysts by sparging nitrogen (4-6 ml/min) through liquid 243db at 10° C. This gave a 0.5-1 ml/min flow of 243db gas. The catalysts were allowed to equilibrate in the HF:243db:$N_2$ (30:0.5-1.0:4-6 ml/min) gas stream for about 1 h before sampling reactor off-gas into a glass burette with DI water for GC analysis. The results are shown in Table 10 below.

TABLE 10

| Example | Catalyst | Temperature/ ° C. | 243db conversion % | 1243yf selectivity % | Pore volume pre test ($N_2$ absorption)/ $cm^3/g$ | Pore volume post test ($N_2$ absorption)/ $cm^3/g$ | Average BJH ads pore diameter pre test/Å | Average BJH ads pore diameter post test/Å |
|---|---|---|---|---|---|---|---|---|
| CE12 | 2% Zn/chrome | 350 | 100 | 23.01 | 0.28 | 0.26 | 92 | 161 |
| CE13 | 4% Zn/chrome | 350 | 100 | 21.45 | 0.25 | 0.19 | 69 | 102 |
| CE14 | 6% Zn/chrome | 350 | 100 | 22.15 | 0.23 | 0.16 | 73 | 153 |
| CE15 | 8% Zn/chrome | 350 | 100 | 20.82 | 0.28 | 0.22 | 93 | 119 |
| CE16 | $Cr_2O_3$ | 350 | 100 | 17.95 | 0.28 | 0.21 | 101 | 167 |
| CE17 | 5.2% Zn/chrome | 350 | 100 | 21.28 | 0.26 | 0.20 | 94 | 113 |
| CE18 | 2.83% Zn/chrome | 350 | 100 | 23.13 | 0.27 | 0.17 | 84 | 128 |
| CE19 | 6% Zn/chrome | 350 | 100 | 21.62 | 0.22 | 0.19 | 54 | 63 |
| CE20 | $Cr_2O_3$ | 350 | 100 | 40.26 | 0.44 | 0.34 | 147 | 261 |
| 21 | 1% Mo/ $Cr_2O_3$ | 350 | 100 | 40.95 | 0.41 | 0.33 | 170 | 287 |
| 22 | 1% Ni/ $Cr_2O_3$ | 350 | 100 | 48.21 | 0.52 | 0.33 | 148 | 232 |
| 23 | 1% Nb/ $Cr_2O_3$ | 350 | 100 | 41.61 | 0.46 | 0.33 | 159 | 338 |

2 wt % graphite was blended with the cooled, calcined catalyst precursor in a waring blender, and the resultant mixture was sieved to <250 μm. The sieved mixture was formed into pellets under a load of 5 tonne in a 32 mm pellet die, 3 g per pellet.

The pellets were then ground to mesh size 0.5-1.4 mm for catalyst testing. Surface area, pore volumes and sizes were measured by $N_2$ adsorption/desorption porosimetry. Ni, Mo and Nb content was measured by X-ray fluorescence spectroscopy.

The performance of these catalysts were tested for the production of 1234yf from the fluorination of 243db and compared to the performance for commercially available chromia catalysts (CE12 to CE19) containing varying quantities of promoter. The pore volumes and diameters for each catalyst were also tested.

An atmospheric pressure screening rig was equipped with four reactor tubes, each with independent HF, organic and nitrogen feeds. The organic feed system was charged with 243db. Each reactor was charged with 2 ml of catalyst with a particle size in the range 0.5-1.4 mm. Initially the nitrogen flow (60 ml/min) was directed to the reactor inlet and the catalysts dried at 200° C. for 2 h.

Following the catalyst drying operation HF vapour was fed to each reactor at a flow of 30 ml/min, diluted with nitrogen (60 ml/min), and passed over the catalysts at 300° C. for approximately 60 minutes until HF was observed in the reactor off gases. At this point the nitrogen flows (reduced to 30 ml/min) were redirected to the reactor exits.

The results show a clear improvement in selectivity for 1234yf when the catalysts of the present invention are utilised. Furthermore, the results show that the catalyst of the invention shows significant pore widening once used, which without wishing to be bound by any theory, may amplify the effect of providing a high pore volume and average pore diameter in the unused catalyst.

Example 24

500 mL deionised water heel was added to a 1.7 L jacketed glass vessel, fitted with an overflow, overhead stirrer, pH probe and thermocouple and cooled to 15° C. The stirrer was actuated at 500 rpm, save for in example 5, where it was turned at 250 rpm.

$Zn(NO_3)_2.6H_2O$ (19.03 g) was dissolved into a solution of $Cr(NO_3)_2(OH)_{(aq)}$ (500 g) in a 600 mL beaker. In another beaker, 500 g 17% $NH_4OH$ solution was provided.

The metal and ammonia solutions were pumped into the chilled water at 5 ml/min. Precipitation of a green/blue solid occurs immediately. The pH of the mixture was monitored and the reactant flow rates adjusted to maintain the target pH for each example as shown in Table 1, below. The reaction was run until all of the metal solution was added.

The slurry was filtered under vacuum until a filter cake formed then washed four times with de-ionised water ("a" examples) or dilute aqueous ammonia solution ("b" examples).

The filter cake was then dried at 105° C. overnight in a standard oven, followed by calcining under flowing nitrogen (200 ml/min) at 300° C. for 12 hours to produce 6.5% ZnO/Cr$_2$O$_3$, the heating rate on the chamber furnace being set to 2° C./min. The percentage mass loss was on calcination was noted.

2 wt % graphite was blended with the cooled, calcined catalyst precursor in a waring blender, and the resultant mixture was sieved to <250 µm. The sieved mixture was formed into pellets under a load of 5 tonne in a 32 mm pellet die, 3 g per pellet.

The pellets were then ground to mesh size 0.5-1.4 mm for catalyst testing. Surface area, pore volumes and sizes were measured by N$_2$ adsorption/desorption porosimetry. Zn content was measured by X-ray fluorescence spectroscopy.

Example 25

500 mL deionised water heel was added to a 1.7 L jacketed glass vessel, fitted with an overflow, overhead stirrer, pH probe and thermocouple and cooled to 15° C. The stirrer was actuated at 411 rpm. A solution of Cr(NO$_3$)$_2$(OH)$_{(aq)}$ (500 g) was measured into a 600 mL beaker plus In(NO$_3$)$_3$.3H$_2$O (13.3 g) and 17% NH$_4$OH solution (318 g) into another beaker. The catalyst was then prepared by the same procedure as Example 24, with a target pH 8.5 and the slurry washed with deionised water (3×600 mL).

Example 26

500 mL deionised water heel was added to a 1.7 L jacketed glass vessel, fitted with an overflow, overhead stirrer, pH probe and thermocouple and cooled to 15° C. The stirrer was actuated at 406 rpm. A solution of Cr(NO$_3$)$_2$(OH)$_{(aq)}$ (500 g) was measured into a 600 mL beaker plus a solution of ZrOCl$_2$.8H$_2$O (13.6 g) in methanol (50 mL) and 17% NH$_4$OH solution (350 g) into another beaker. The catalyst was then prepared by the same procedure as Example 24, with a target pH 8.5 and the slurry washed with deionised water (3×600 mL).

Production of 1234yf and 245cb from 1233xf

The performance of the catalyst of Examples 24 to 26 was tested for the production of 1234yf and 245cb from the fluorination of 1233xf by contact with HF. The results were compared to those of a commercially available chromia catalyst (Comparative Example 27) and a commercially available Zn doped chromia catalyst (Comparative Example 28).

Each catalyst (3 mL, 0.5-1.4 mm) was charged to an 0.5" OD Inconel 625 reactor supported by Inconel mesh. The catalysts were dried at 250° C. under 60 mL/min flowing nitrogen for at least 2 hours prior to pre-fluorination. HF vapour flowing at 30 ml/min was then passed over the catalyst along with 30 ml/min nitrogen at 250° C. for one hour. The nitrogen was then directed to the reactor exit leaving neat HF passing over the catalyst. The temperature was slowly ramped to 380° C. and held for 10 hours. The temperature was then reduced to 350° C. and the HF flow reduced to 25 mL/min. A co-feed of 1233xf (2-chloro-3,3,3-trifluoropropene) was fed by its own vapour pressure and the flow controlled to 1 mL/min through an orifice plate. Reactor off-gas was sampled periodically from 0.5 to 7 h of continuous running, into deionised water and analysed by GC to determine reaction progress. Results are shown in Table 11.

TABLE 11

| Example Catalyst | Pore Volume @0.99P/P° (cm$^3$/g) | Average. BJH Ads Pore Diameter (Å) | Activity 1233xf Conv. (%) | Product Yield 1234yf mol (%) | Product Yield 245cb mol (%) | Conv. Decay rate (Stability) k (h$^{-1}$) | Conv. Half-life (Stability) t$_{0.5}$ (h) | Conv. Half-life (Stability) t$_{0.5}$ (h · g$^{-1}$) |
|---|---|---|---|---|---|---|---|---|
| CE27 | 0.284 | 101 | 27.8 | 18.8 | 5.4 | 0.13 | 5.6 | 2 |
| CE28 | 0.288 | 90 | 76.2 | 44.9 | 13.0 | 0.33 | 2.1 | 0.7 |
| 24 | 0.606 | 205 | 70.9 | 50.8 | 13.6 | 0.13 | 5.5 | 3.4 |
| 25 | 0.563 | 122 | 62.5 | 45.2 | 12.2 | 0.05 | 13.2 | 10.1 |
| 26 | 0.516 | 123 | 36.5 | 25.9 | 7.7 | 0.1 | 6.9 | 4.6 |

It appears from the data in Table 11 that the addition of promoters to the base chromia catalysts increased their activity compared to the unpromoted reference catalyst of Comparative Example 27. It also appears that by increasing both pore volume and pore diameter and adding a zinc promoter it was possible to produce a catalyst such as of (Example 24) that was comparable in activity terms but was more selective and stable than the catalyst of Comparative Example 28.

Production of 1234yf from 245cb

The performance of the catalyst of Examples 24 and 25 was tested for the production of 1234yf from the dehydrofluorination of 245cb. The results were compared to those of a commercially available chromia catalyst (Comparative Example 29) and a commercially available zinc promoted chromia catalyst (Comparative Example 30).

Each catalyst (3 mL, 0.5-1.4 mm) was charged to an 0.5" OD Inconel 625 reactor supported by Inconel mesh. The catalysts were dried at 250° C. under 60 mL/min flowing nitrogen for at least 2 hours prior to pre-fluorination. HF vapour flowing at 30 mL/min was then passed over the catalyst along with 30 mL/min nitrogen at 250° C. for one hour. The nitrogen was then directed to the reactor exit leaving neat HF passing over the catalyst. The temperature was slowly ramped to 380° C. and held for 10 hours. The temperature was then reduced to 250° C. and the HF flow reduced to 25 mL/min. A co-feed of 245cb (1,1,1,2,2-pentafluoropropane) vapour was fed by sparging nitrogen (1 mL/min) through the liquid at 9° C. and resulting in a 245eb flow of 1 mL/min. Reactor off-gas was sampled periodically from 0.5 to 7 h of continuous running into deionised water and analysed by GC to determine reaction progress. Results are shown in Table 12.

TABLE 12

| Example Catalyst | Mass/g | Pore Volume @0.99P/P° (cm³/g) | Average. BJH Ads Pore Diameter (Å) | Initial Activity 245cb Conversion (%) | Initial Yield 1234yf mol (%) |
|---|---|---|---|---|---|
| CE29 | 2.7 | 0.284 | 101 | 78.5 | 76.3 |
| CE30 | 2.9 | 0.288 | 90 | 80.1 | 71.4 |
| 24 | 1.7 | 0.606 | 205 | 79.3 | 77.0 |
| 25 | 1.4 | 0.563 | 122 | 80.6 | 72.8 |

It appears from by the results shown in Table 12 that the catalyst activity is increased by promoting the chromia with Zn and In. Increasing the pore volume and average pore diameter of the Zn-promoted chromia also increased the yield of 1234yf.

Production of 1234yf from 245eb

The performance of the catalyst of Examples 24 to 26 was tested for the production of 1234yf and 245cb from the dehydrofluorination of 245eb. The results were compared to those of a commercially available chromia catalyst (Comparative Example 31) and a commercially available zinc promoted chromia catalyst (Comparative Example 32).

Each catalyst (3 mL, 0.5-1.4 mm) was charged to an 0.5" OD Inconel 625 reactor supported by Inconel mesh. The catalysts were dried at 250° C. under 60 mL/min flowing nitrogen for at least 2 hours prior to pre-fluorination. HF vapour flowing at 30 mL/min was then passed over the catalyst along with 30 mL/min nitrogen at 250° C. for one hour. The nitrogen was then directed to the reactor exit leaving neat HF passing over the catalyst. The temperature was slowly ramped to 380° C. and held for 10 hours. The temperature was then reduced to 250° C. and the HF flow reduced to 25 mL/min. A co-feed of 245eb (1,1,1,2,3-pentafluoropropane) vapour was fed by sparging nitrogen (1 mL/min) through the liquid at 9° C. and resulting in a 245eb flow of 1 mL/min. Reactor off-gas was sampled periodically from 0.5 to 7 h of continuous running into deionised water and analysed by GC to determine reaction progress. The results are shown in Table 13.

TABLE 13

| Example Catalyst | Mass/g | Pore Volume @0.99P/P° (cm³/g) | Average. BJH Ads Pore Diameter (Å) | Activity 245eb Conversion (%) | Rate of increase in activity 245eb Conversion gain (%/h) | Yield 1234yf mol (%) | Selectivity 1234yf mol (%) |
|---|---|---|---|---|---|---|---|
| CE31 | 2.7 | 0.284 | 101 | 18.7 | 0.5 | 15.3 | 81.6 |
| CE32 | 2.9 | 0.288 | 90 | 36.3 | 0.9 | 21.6 | 59.3 |
| 24 | 1.7 | 0.606 | 205 | 13.6 | 0.3 | 11.5 | 85.2 |
| 25 | 1.4 | 0.563 | 122 | 17.9 | 4.7 | 15.0 | 83.8 |
| 26 | 1.4 | 0.516 | 123 | 11.8 | 3.1 | 10.7 | 90.2 |

As shown by the results in Table 13, increasing the pore volume and average pore diameter of the Zn-promoted chromia (Example 24) led to increased selectivity to 1234yf. Likewise promotion with In and Zr plus increasing the pore volume and average pore diameter also increased the selectivity to 1234yf.

Preferences and options for a given aspect, feature or parameter of the invention should, unless the context indicates otherwise, be regarded as having been disclosed in combination with any and all preferences and options for all other aspects, features and parameters of the invention.

The invention claimed is:

1. A fluorination catalyst comprising at least 80 wt % chromia and at least one additional metal or compound thereof, wherein the catalyst does not comprise Ni, Pd, Al or Pt, wherein the catalyst has a total pore volume of greater than 0.4 cm³/g and a mean pore diameter greater than or equal to 90 Å, and wherein the total pore volume is measured by $N_2$ adsorption porosimetry and the mean pore diameter is measured by $N_2$ BET adsorption porosimetry.

2. The catalyst according to claim 1, wherein the mean pore diameter of the catalyst is greater than or equal to 100 Å when measured by $N_2$ BET adsorption porosimetry.

3. The catalyst according to claim 1, wherein the mean pore diameter of the catalyst is greater than or equal to 130 Å when measured by $N_2$ BJH adsorption porosimetry.

4. A The catalyst according to claim 1, wherein the mean pore diameter of the catalyst is greater than or equal to 90 Å when measured by $N_2$ BJH adsorption porosimetry.

5. The catalyst according to claim 1 provided in the form of a pellet or pellets comprising a plurality of catalyst particles.

6. The catalyst according to claim 5, wherein the pellets comprise graphite, in an amount of from about 0.5 wt % to about 10 wt %.

7. The catalyst according to claim 5, wherein the pellets have a longest dimension from about 1 mm to about 100 mm.

8. The catalyst according to claim 1, wherein the at least one additional metal or compound thereof is a transition metal.

9. The catalyst according to claim 8, wherein the transition metal is zinc.

10. The catalyst according to claim 1, wherein the catalyst is unused.

11. A method of preparing the catalyst as defined in claim 1, comprising the steps of:
 a) preparing a metal solution and a hydroxide solution;
 b) combining the solutions at a pH of greater than 8 in order to precipitate a metal hydroxide(s);
 c) drying the precipitated metal hydroxide(s); and
 d) calcining the metal hydroxide(s) to form the metal oxide(s).

12. The method according to claim 11, wherein step b) is carried out at a pH of greater than or equal to 8.5.

13. The method according to claim 11, wherein the metal salt comprises a nitrate salt such as a hydroxide nitrate salt.

14. The method according to claim 11, wherein the hydroxide solution comprises ammonium hydroxide ($NH_4OH$).

15. The method according to claim 11, wherein the metal salt solution is provided at a concentration of from about 1 mol/l to about 10 mol/l.

16. The method according to claim 11, wherein the hydroxide solution is provided at a concentration of from 1 mol/l to about 10 mol/l.

17. The method according to claim 11, wherein step (b) is performed by combining the solutions in a body of solvent.

18. The method according to claim 11, wherein step (b) is carried out at a substantially constant temperature.

19. The method according to claim 11, wherein step (b) is performed while agitating the combined solutions.

20. The method according to claim 11, wherein the precipitate formed during step (b) comprises particles having average longest dimensions of from about 5 μm to about 20 μm.

21. The method according to claim 11, wherein step (c) comprises removing liquid from the slurry of metal hydroxide precipitate(s) to produce a wet cake.

22. The method according to claim 21, wherein the cake is washed prior to any drying or calcining.

23. The method according to claim 21, wherein step (c) comprises removing liquid from the wet metal hydroxide(s) cake by exposing it to an elevated temperature between 50° C. and 200° C.

24. The method according to claim 23, wherein the precipitate is exposed to the elevated temperature for at least 15 mins.

25. The method according to claim 11, wherein step (d) comprises a step of calcining the metal hydroxide(s), after liquid removal and/or drying.

26. The method according to claim 11, wherein the calcining step comprises heating the metal hydroxide(s) to a temperature between about 200° C. and about 550° C.

27. The method according to claim 11, wherein the calcining step is performed for a sufficient period to produce a catalyst having a TGA loss on ignition (LOI) of less about 15.

28. The method according to claim 11 further comprising combining the calcined metal oxide with graphite to provide a catalyst composition comprising about 0.1 wt % to around about 10 wt % graphite.

29. The method according to claim 11, wherein the calcined metal oxide and/or catalyst composition is pressed to form catalyst pellets.

30. The method according to claim 29, wherein the pressing takes place under a load of about 1 to 100 tonnes.

31. The method according to claim 30, wherein the pellets so formed have a longest dimension from about 1 mm to about 100 mm.

32. A process for fluorinating a $C_{2-3}$ hydrohalocarbon species, comprising contacting the species with the catalyst according to claim 1.

33. The process according to claim 32, comprising contacting trichloroethylene with the catalyst in the presence of HF to produce 1,1,1,2-tetrafluoroethane (134).

34. The process according to claim 32 wherein the species is a $C_3$ hydrohalocarbon species.

35. The process according to claim 32, wherein the process is conducted in the vapour phase.

36. A process for dehydrohalogenating $C_{2-3}$ hydrohalocarbon species, comprising contacting the species with the catalyst according to claim 1.

37. The process according to claim 36 wherein the species is a $C_3$ hydrohalocarbon species.

38. The process according to claim 36, comprising contacting a hydro(halo)fluoropropane with the catalyst to produce a fluoropropene.

39. The process according to claim 36, wherein the fluoropropene is a tetrafluoropropene (1234).

40. The process according to claim 39, wherein the hydro(halo)propane comprises a compound selected from the group consisting of: 1,1,1,2,3-pentafluoropropane, 1,1,1,2,2-pentafluoropropane and/or 1,1,1,3,3-pentafluoropropane.

41. The process according to claim 39, wherein the tetrafluoropropene comprises 1,3,3,3-tetrafluoropropene and/or 2,3,3,3-tetrafluoropropene.

42. A process for manufacturing a tetrafluoropropene comprising contacting a hydro(halo)propene with HF in the presence of the catalyst according to claim 1.

43. The process according to claim 42, wherein the hydro(halo)propene comprises a hydrochlorofluoropropene.

44. A process for eliminating HF from a saturated $C_{2-3}$ hydrohalocarbon species, comprising contacting the species with a the catalyst according to claim 1.

45. A process for adding HF to an unsaturated $C_{2-3}$ hydrohalocarbon species, comprising contacting the species with the catalyst according to claim 1.

46. A fluorinated catalyst according to claim 1.

* * * * *

UNITED STATES PATENT AND TRADEMARK OFFICE
CERTIFICATE OF CORRECTION

PATENT NO. : 11,406,965 B2
APPLICATION NO. : 16/331259
DATED : August 9, 2022
INVENTOR(S) : Claire Nicola Rees et al.

It is certified that error appears in the above-identified patent and that said Letters Patent is hereby corrected as shown below:

In the Claims

Column 18, Claim 4, Line 16, delete "A".

Column 18, Claim 8, Line 29, delete "thereof".

Column 19, Claim 27, Line 34, insert --than-- between "less" and "about".

Column 19, Claim 28, Line 38, delete "around".

Column 20, Claim 33, Line 9, delete "(134)" and insert in its place --(134a)--.

Column 20, Claim 36, Line 14, insert --a-- between "dehydroalogenating" and "$C_{2-3}$".

Column 20, Claim 44, Line 39, delete "a".

Signed and Sealed this
Eighteenth Day of October, 2022

Katherine Kelly Vidal
*Director of the United States Patent and Trademark Office*